United States Patent [19]
Martin et al.

[11] Patent Number: 5,409,644
[45] Date of Patent: Apr. 25, 1995

[54] CATHETERS AND METHOD OF MANUFACTURE

[75] Inventors: Geoffrey S. Martin; Mahase Nardeo, both of Mississauga, Canada

[73] Assignee: Med-Pro Design, Inc., Mississauga, Canada

[21] Appl. No.: 136,855

[22] Filed: Oct. 18, 1993

Related U.S. Application Data

[63] Continuation of Ser. No. 955,802, Oct. 2, 1992, abandoned.

[51] Int. Cl.$^6$ .................... B29C 33/02; B29C 41/02; B29C 41/46
[52] U.S. Cl. ...................... 264/25; 264/296; 264/322; 264/323
[58] Field of Search ............... 264/25, 296, 322, 323

[56] References Cited

U.S. PATENT DOCUMENTS

| | | | |
|---|---|---|---|
| 4,404,159 | 9/1983 | McFarlane | 264/296 |
| 4,961,809 | 10/1990 | Martin | 264/322 X |
| 5,135,599 | 8/1992 | Martin et al. | 264/322 X |

Primary Examiner—Leo B. Tentoni
Attorney, Agent, or Firm—Rogers & Scott

[57] ABSTRACT

In one of its aspects, the invention provides a catheter of a selected length, and having a main body of a first cross-section and a tip section of smaller cross-section, the tip section being formed integrally with the main body from a catheter blank having a length less than the selected length. Also, in another of its aspects, the invention provides a method of making a catheter tip on a main body of thermoplastic synthethic plastics material and having a first cross-section. A progressive forming technique is used to reduce the cross-section of the body to create a tip section of smaller cross-section.

1 Claim, 2 Drawing Sheets

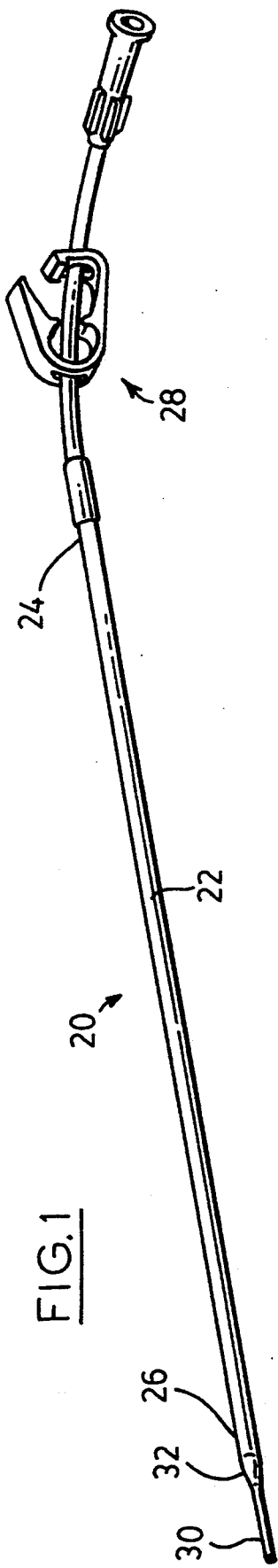
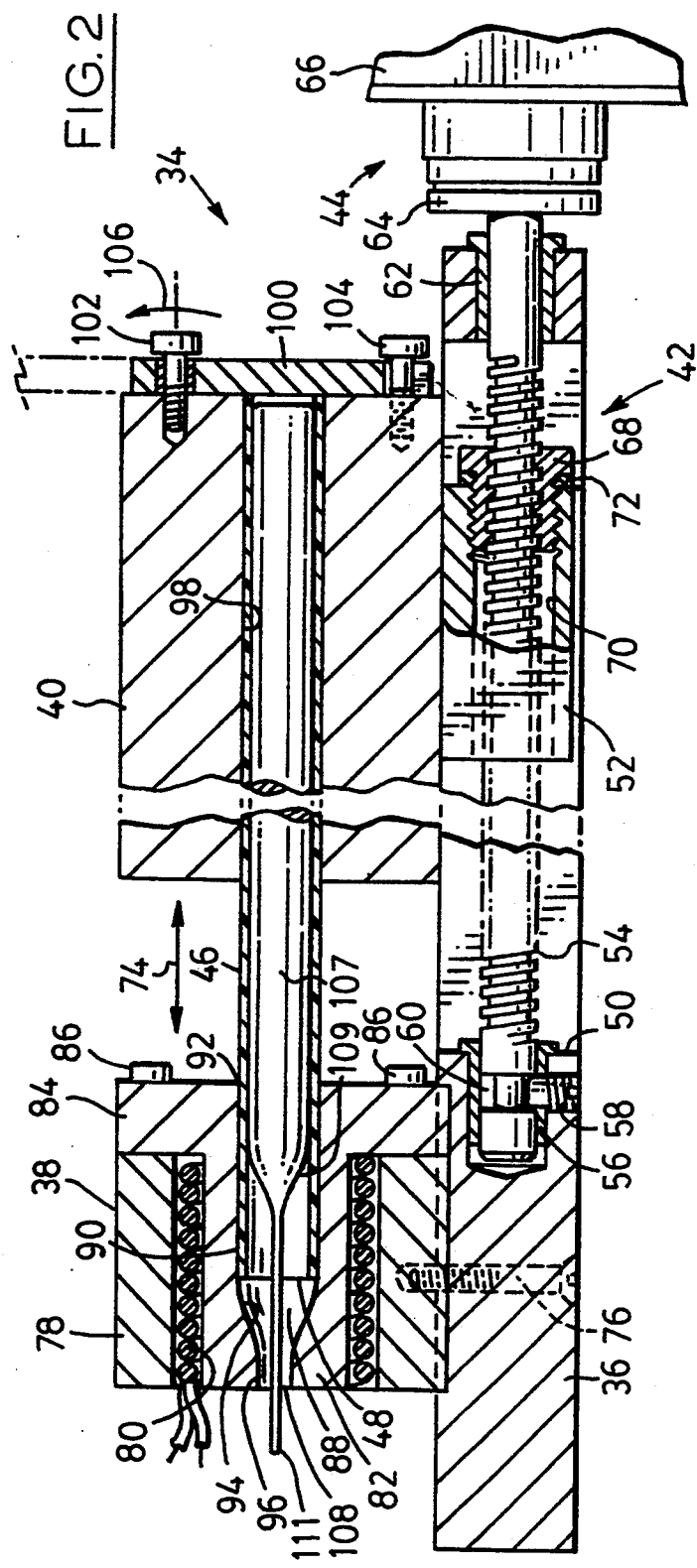

CATHETERS AND METHOD OF MANUFACTURE

This is a Continuation of application Ser. No. 07/955,802 filed Oct. 2, 1992, now abandoned.

This invention relates to catheters and more particularly to a tip portion formed on the distal end of a catheter, and to the method of manufacturing catheters having tip sections.

BACKGROUND OF THE INVENTION

There are many forms of catheter and the shapes and sizes are dictated primarily by use, requirements for insertion, whether the catheter is for long or short term use, and other similar factors. Within these many forms is a group of catheters which are designed to be entered into a blood vessel. Such intrusion is becoming increasingly more common as techniques and procedures for dialysis, angioplasty, and cardiac treatments improve. In such procedures the catheter is entered into the blood vessel using one of a number of different techniques.

A first of these techniques is known as a cut-down technique. In this procedure the tissue is parted and the blood vessel opened surgically to enter the catheter. Other techniques involve the use of a hollow needle. In one approach the needle is followed by a sleeve and the catheter is engaged within the sleeve which is then removed. Another technique was developed by Seldinger and this involves the use of a wire which is engaged through the hollow needle to guide the catheter into position.

Catheters in blood vessels should preferably have a configuration of tip portion which minimizes the risk of damage to the blood vessel. The portion is preferably shaped to have a reduced cross-section compared with the main body of the catheter and is configured with a less rigid section adjacent the tip to permit the catheter to flex to the shape of the blood vessel. It is not uncommon to arrange the catheter to have a main body of a first cross-section and a tip portion of a smaller cross-section so that on insertion the smaller cross section can be entered and act as a flexible guide for the larger cross-section.

When it is required to make a catheter with a smaller cross-section at the tip, it has become practice to provide a section of thermoplastic material of the required cross-section and to attach this to the main body which is also of thermoplastic material. This approach, while proving to be satisfactory, must be policed very carefully to ensure adequate quality control since separation of the parts is clearly unacceptable. As a result, the complexity of manufacture and the requirements for care and to ensure proper quality all add to the cost and complexity of the product.

This need related to catheters designed for intrusion into a blood vessel demonstrates the general need for a catheter having a tip of reduced cross-section of integral construction. Also a method of manufacture is needed which will permit a tip section of smaller cross-section to be formed integrally from part of the main body in a controlled manner so that the product is readily reproduced within acceptable tolerances.

SUMMARY OF THE INVENTION in one of its aspects, the invention provides a catheter of a selected length, and having a main body of a first cross-section and a tip section of smaller cross-section, the tip section being formed integrally with the main body from a catheter blank having a length less than the selected length. Also, in another of its aspects, the invention provides a method of making a catheter tip on a main body of thermoplastic synthethic plastics material and having a first cross-section. A progressive forming technique is used to reduce the cross-section of the body to create a tip section of smaller cross-section.

BRIEF DESCRIPTION OF THE DRAWINGS

The invention will be better understood with reference to the drawings taken in combination with the following description, in which:

FIG. 1 is an isometric view of an exemplary catheter made in accordance with the invention;

FIG. 2 is a schematic side sectional view of apparatus used to make the catheter and shown in a position prior to forming a tip section;

DESCRIPTION OF THE PREFERRED EMBODIMENTS

Figure 3:
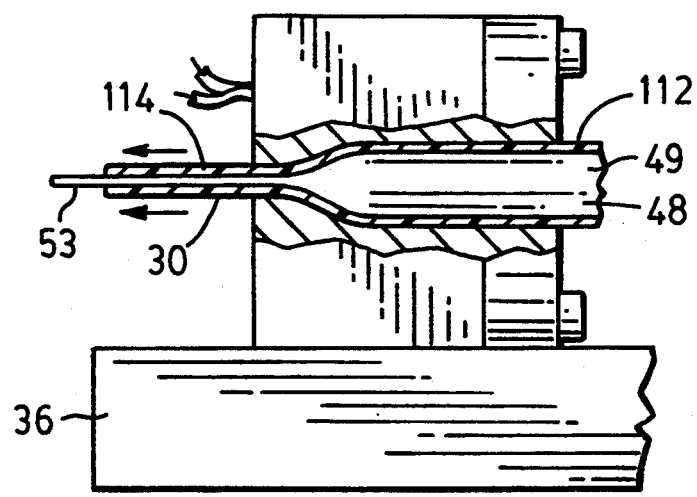
FIG. 3 is a fragmentary view showing the portion of the structures shown in FIG. 2 and illustrating the position after the tip section has been formed.

Reference is made firstly to FIG. 1 which illustrates an exemplary catheter designated generally by the numeral 20 and consisting of a main body 22 which extends from a proximal end designated by the numeral 24 to a distal end designated by the numeral 26. Proximal end structure 28 is provided to make attachment to the main body 22 and is of conventional form. At the other end, a tip section 30 is provided and connected to the main body 22 by a transitional portion 32. The material of the tip section defines a smaller cross-sectional area than the material of the cross-section of the main body, and the transitional portion 32 blends smoothly both internally and externally from the main body to the tip section.

As will become evident, the external cross-sectional shape of the tip section 30 is constant although post-forming to taper the tip section, at least partially, is of course possible according to accepted practice in the art.

Reference is next made to FIG. 2 which illustrates apparatus designated generally by the numeral 34 and consisting essentially of a bed plate 36 to which is attached a die assembly 38 which can be heated for forming the tip section as will be described, and a carriage 40 which can be driven along the bed plate 36 by a transport mechanism 42 operated by a drive 44.

As will be described in more detail, the carriage 40 contains a catheter blank 46 of thermoplastic synthetic plastics material and within that is a heat resistant mandrel 48 preferably of stainless steel. The mandrel has a cylindrical main portion 49 which tapers forwardly to a small diameter extension 53. The blank has a cross-section and wall thickness corresponding with those dimensions required in-the finished main body 22 (FIG. 1). The die assembly 38 receives the blank which can be progressed into and through the die by the drive 44 operating the transport mechanism 42.

The bed plate 36 defines a central slot 50 shaped to contain a tongue 52 attached to the underside of the carriage 40 and forming part of the carriage. The slot 50 contains parts of the transport mechanism 42 and in particular a square threaded shaft 54 contained at one end in a bushing 56 which is located by a set screw 58 in the plate 36. The set screw has a plain end engaged in a groove 60 in the shaft 54. At its other end, the shaft is mounted in a plain bushing 62 also located in the plate, and is driven through a slipping clutch 64 by a mechanism 66 forming part of the drive 44. This can be any conventional drive operable to rotate the shaft 54 in both directions as required.

The transport mechanism 42 is completed by a threaded sleeve 68 which is engaged in a bore 70 of the tongue 52. The sleeve has a head for engaging and tightening the sleeve with a lock washer 72 to maintain the assembly.

It will be evident that the arrangement of the transport mechanism 42 and drive 44 is such that when the mechanism 66 is operated, drive through the clutch rotates the shaft 54 which, because it is located in the plate, transmits longitudinal motion to the tongue 52 and hence to the whole carriage 40. The arrangement is therefore such that the carriage can be made to move longitudinally in the directions indicated by arrow 74, i.e. towards and away from the die assembly 38.

The die assembly 38 is mounted by set screws 76 (one of which is seen in FIG. 2) and located on the bed plate 36 for alignment with the carriage 40 as will be described. The die has a housing 78 containing a cylindrically wound heating element 80 which is positioned between the housing 78 and a die 82. An end flange 84 on the die 82 is proportioned so that bolts 86 can be used to assemble the die to the housing 78.

The die defines an axially extending opening designated generally by the numeral 88 and consisting of a cylindrical entry portion 90 extending from an entrance 92 to a convergent intermediate portion 94 which extends smoothly from the entry portion 90 and terminates at a short exit portion 96 which is cylindrical and which defines the cross-section of the tip to be made as will be described with reference to FIG. 3.

The carriage 40 defines a cylindrical opening 98 proportioned to receive the catheter blank 46 and the opening 98 is axially aligned with the opening 88 in the die 82. At the entry end of the opening 98 in the carriage, a swing door 100 is provided rotatable about bolt 102 for engagement with a bolt 104 which sits in a slot in the door 100 in conventional fashion. When the door is opened it is generally in the position shown in ghost outline having been moved through the direction of the arrow 106. This permits entry of the blank 46 which is engaged while containing the mandrel 48. The mandrel has a main part 107 having the same cross-section as the internal cross-section of the main body 22, a converging part 109 blending into the part 107, and a leading part 111 also blends into the converging part 109 and has an external cross-section corresponding to the desired internal shape of the tip section 30. It should be noted that this part of the mandrel should preferably have a length sufficient to accommodate the increase in length of the catheter blank which will take place during the forming process. This will ensure support for the full length of the tip section after forming through the die. The parts of the mandrel blend into one another to give a smooth internal surface to the finished catheter.

The mandrel and blank are pushed into position until the door can be closed and the leading end of the blank 46 will be in the position shown in FIG. 2 with the mandrel extending beyond the blank.

With the assembly shown and the die heated, the drive 44 is actuated to move the carriage 40 to the left (as drawn) which will drive the blank 46 into the intermediate portion 94 of the opening 88 and thence to the exit portion 96 before material from the blank leaves through an exit 108. This will continue until the position illustrated in FIG. 3 is reached where the mandrel has been driven to the point where it complements the shape of the opening 88. This is because the converging part 109 of the mandrel has a shape corresponding to the required internal shape which matches generally the shape of the intermediate portion 94 (FIG. 2) of the opening 88 in the die so that when the position shown in FIG. 3 is reached, the resistance to further movement of the carriage is such that the clutch 64 will slip and the operator is aware that the movement has been completed.

After suitable cooling, the molded catheter can be removed and it will have the shape illustrated in cross-section in FIG. 3.

In general, and as seen in FIG. 3, an outer wall of the catheter blank 112 is supported by the mandrel and carriage to minimize the risk of buckling during the forming process. Also, where thin walled blanks are used, it will be desirable to arrange the proportions of the die and mandrel so that the tip section 30 has a wall 114 of thicker cross-section than the wall 112. There will be a transition between these two walls defined by the mandrel and the opening at the intermediate portion 94 (FIG. 2). Also, it may well be that the proportions of the blank and the distance travelled etc. are such that a full mandrel of the type shown in FIG. 2 is not necessary to support the wall. Nevertheless, it is desirable that the mandrel be arranged to give proper support at the transition portion and to ensure proper shaping of the catheter at this point. It is also convenient from the standpoint of increasing the resistance to motion so that the clutch 64 will operate only when the complete forming has taken place. The same result could be achieved however by a measuring procedure with a mandrel that is of constant diameter such as the end portion 110. Again, this would depend upon the plastics being used, the rate at which the forming is being done, the side wall, etc.

The amount of material per unit of length will be less in the tip section 30 than in the main body 22 due to the reduction in cross-sectional area of the material during the forming procedure. This will result in a catheter which is larger than the catheter blank 46. Also, because a compressive forming technique is being used, the density of the material in the tip section 30 will tend to be greater than the density of the material in the main body. These factors must be taken into consideration in designing the flexibility of the tip section relative to that of the main body.

Also, it is noteworthy that the process used distinguishes the resulting product due to the change in density achieved while maintaining the integrity of the original catheter blank. This obviates the need for a separate bonded tip to achieve similar results and consequently the catheter is simpler to make and has no likelihood of failure by separation of parts, as is the case when the catheter is made from several pieces. Such improvements in the art flow from the present invention.

It is also within the scope of the invention to accommodate different cross-sections of catheter and, with variations, it is possible to shape in this way catheters that have multiple lumens. Each of the lumens would be supported by mandrels such as mandrel 48 and the mandrels would extend as far as it is required that the lumen extend. It is conventional in multi-lumen structures for one of the lumens to extend to the end of the catheter and consequently one of the mandrels would do this while the others would fall short of the end. Some cutting of the blank in the region where the tip is to be formed may be beneficial to minimize the amount of plastic flow required, but the process nevertheless would follow the same characteristics as that described with reference to the exemplary embodiment shown in FIGS. 1 to 3.

As mentioned previously, a catheter made according to this invention can be post-formed to create a tapered tip at the end of the tip section. Other such changes include adding side openings, bending the catheter and generally creating variations from the basic catheter described here. It is also within the scope of the invention to tailor the flexibility of the tip section relative to the stiffness of the main body in a selected ratio by forming the wall thickness of the tip portion appropriately. Some trial and error may of course be used to develop experience with a particular die, catheter form, etc.

These and other catheters and methods of manufacture are within the scope of the invention as claimed.

We claim:

1. A method of forming a catheter from thermoplastic materials, the catheter being of a selected length and extending axially between proximal and distal ends, the catheter having a main body extending from the proximal end and being of a first cross-section, a tip section extending towards the main body from the distal end and having a constant cross-section smaller than said first cross-section, and a transition portion between the main body and the tip section and which blends smoothly into both the main body and the tip section, the method comprising the steps:

providing a die having an opening extending about a die axis, the opening having an entry portion extending inwardly from an entrance and having a cross-section corresponding to that of the main body of the catheter, a convergent intermediate portion blending into the entry portion, and an exit portion having said smaller cross-section and also blending smoothly into the intermediate portion, the exit portion terminating at an exit;

providing heating means coupled to the die to elevate the die temperature to a temperature selected to cause plastic flow of the catheter material;

providing a heat resistant mandrel having a leading part, a converging part leading smoothly from the tip section and a main part extending smoothly from the converging part;

providing a tubular blank of catheter material having an outside shape corresponding to that of said main body and an internal shape corresponding to the shape of the main part of the mandrel so that the mandrel will slide into the blank, the blank having an entry end and a tip end having a length less than said selected length;

entering the leading part of the mandrel into the blank from said entry end and moving the mandrel through the blank until some of the leading part projects beyond said tip end of the blank;

operating the heating means to maintain the die at said selected temperature;

retaining the mandrel and blank together as a combination and causing relative movement axially between this combination and the die so that the tip end is first through said entrance of the die;

continuing said relative movement thereby causing the entry end of the blank to pass through the exit portion and to project beyond said exit causing the material of the blank to flow axially to create said tip section and thereby lengthen the blank, said relative motion continuing until the converging part of the mandrel and the intermediate portion of the die are separated by an amount to define the transition portion of the catheter;

removing the catheter from the die and removing the mandrel from the catheter whereby a catheter is formed having a length greater than that of the blank and including said tip section, transitional portion, and main body.

* * * * *